United States Patent [19]
Morandi et al.

[11] Patent Number: 6,093,019
[45] Date of Patent: *Jul. 25, 2000

[54] DENTAL IMAGING SYSTEM WITH DIGITAL MOTION VIDEO

[75] Inventors: James W. Morandi, Camarillo, Calif.; Douglas A. Golay, Coon Rapids, Iowa

[73] Assignee: Integra Medical, Camarillo, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/996,982

[22] Filed: Dec. 23, 1997

[51] Int. Cl.[7] .................................................. A61C 3/00
[52] U.S. Cl. ............................................................ 433/29
[58] Field of Search ....................................... 433/29, 229

[56] References Cited

U.S. PATENT DOCUMENTS

| | | | |
|---|---|---|---|
| 4,952,149 | 8/1990 | Duret et al. | 433/229 |
| 5,278,756 | 1/1994 | Lemchen et al. | 600/587 |
| 5,367,337 | 11/1994 | Pyle et al. | 348/521 |
| 5,661,519 | 8/1997 | Franetzki | 433/29 |
| 5,766,006 | 6/1998 | Murljacic | 433/26 |

*Primary Examiner*—John J. Wilson
*Attorney, Agent, or Firm*—Blakely Sokoloff Taylor & Zafman LLP

[57] ABSTRACT

A dental imaging system that extracts still images from a digital movie of a patient's mouth. The system allows still images free of shakes or flutter to be taken using an intraoral camera at the desired angle more easily than using conventional still image capture systems which may require several retakes before realizing a flutter-free image at the correct angle. Another embodiment uses image processing techniques, including color filtering and edge detection, to automatically and rapidly detect teeth in an image of a patient's mouth, without having to manually define the outline of each tooth.

10 Claims, 6 Drawing Sheets

DENTAL IMAGING SYSTEM WITH DIGITAL MOTION VIDEO

BACKGROUND

This invention is generally related to dental imaging systems and more particularly to systems that support digital motion video.

Dental imaging systems have been used for a number of years to assist the dentistry professional in recording images of a patient's mouth. Conventional systems include the analog video camera and video cassette recorder (VCR) combination and, more recently, digital still image capture systems. Both systems use a miniature camera known as an intraoral camera that is inserted into the patient's mouth to capture images of teeth and gums. At the same time, the images are being displayed which allows the dentist as well as perhaps the patient to view the treatment areas in a more comfortable manner.

With the analog VCR system, the dentist can create a movie of the patient's mouth. Although the movie is a useful feature both from a diagnosis standpoint and from a patient understanding point of view, dentists often only need to store a still image of the treatment areas for their patient records. The VCR system, however, is not an effective means for providing still images, primarily because of the well-known "shakes" that often appear on the display when the movie is paused. Moreover, a VCR-based system does not provide for easy indexing, access, and manipulation of the still images.

The digital still image capture system has solved some of the problems in the older VCR-based systems by providing digital still images that can be easily stored and manipulated using a personal computer (PC). However, shakes or flutter in the still image are still a problem, particularly because the smallest movement between the intraoral camera (which has a high magnification) and the patient's mouth can cause the scene to change dramatically while a single still image is being captured. The dentist may need to hold the camera very still for several retakes until an acceptable quality still image is captured. This is an undesirable burden. Moreover, although the system can create still images, the creation of movies will require a separate VCR-based system. This dual requirement is a financial and practical burden which has not helped promote dental imaging systems in the past.

In view of the above, there is a need for a novel dental imaging system that can reduce the incidence of shakes in digital still images and still provide a cost effective movie solution.

The use of digital still images has also allowed image manipulation techniques to be used in illustrating the visual effects of cosmetic treatments on a patient's mouth and teeth prior to the treatments actually being performed on the patient. With conventional techniques, the outline of the teeth are manually marked off on the image. However, because of the need to carefully delineate the teeth boundary (so as to obtain a more realistic representation of the treatment to be performed), the manual technique is often too time consuming, thus precluding its performance while the patient waits in the operatory. Therefore, there is also a need for a faster tooth detection technique.

SUMMARY

The invention is directed at computer-implemented methods of dental imaging. A computer system is used to record digital motion image data and display a corresponding digital movie of a patient's oral site. Data representing a still image of the site is selected from the motion image data. The motion image data is acquired at a rate that is sufficiently high so as to require maybe at most one frame advance or rewind in order to obtain a still image having the desired angle and being free of shakes.

Another embodiment of the invention is directed at using image processing techniques, including color filtering and edge detection, to automatically detect teeth in an image of a patient's mouth, without having to manually define the teeth.

DETAILED DESCRIPTION

As summarized above, some of the embodiments of the invention are directed at a computer-implemented method of dental imaging that provides digital motion images, and shake-free still images of a patient's mouth that are extracted from the motion images. Using digital motion images to derive the still images allows the user to easily vary and select the angle of the still images while a movie of the patient's mouth is being recorded. The patient can also be given a movie tour of her mouth and teeth by rotating and moving the camera around the mouth and teeth to achieve a pleasant 3-D effect. Once the movie and still images have been acquired, they can be stored with associated patient identification and other information in a database for easy access at a later time.

In another embodiment, the invention provides steps to be performed by a computer system in automatically detecting the teeth and gums of the patient based on a still image of the patient's mouth.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

For purposes of explanation, specific embodiments are set forth below to provide a thorough understanding of the invention. However, as understood by one skilled in the art, from reading this disclosure, the invention may be practiced without such details. Furthermore, well-known elements, devices, process steps, and the like, are not set forth in detail in order to avoid obscuring the invention.

Figure 1:
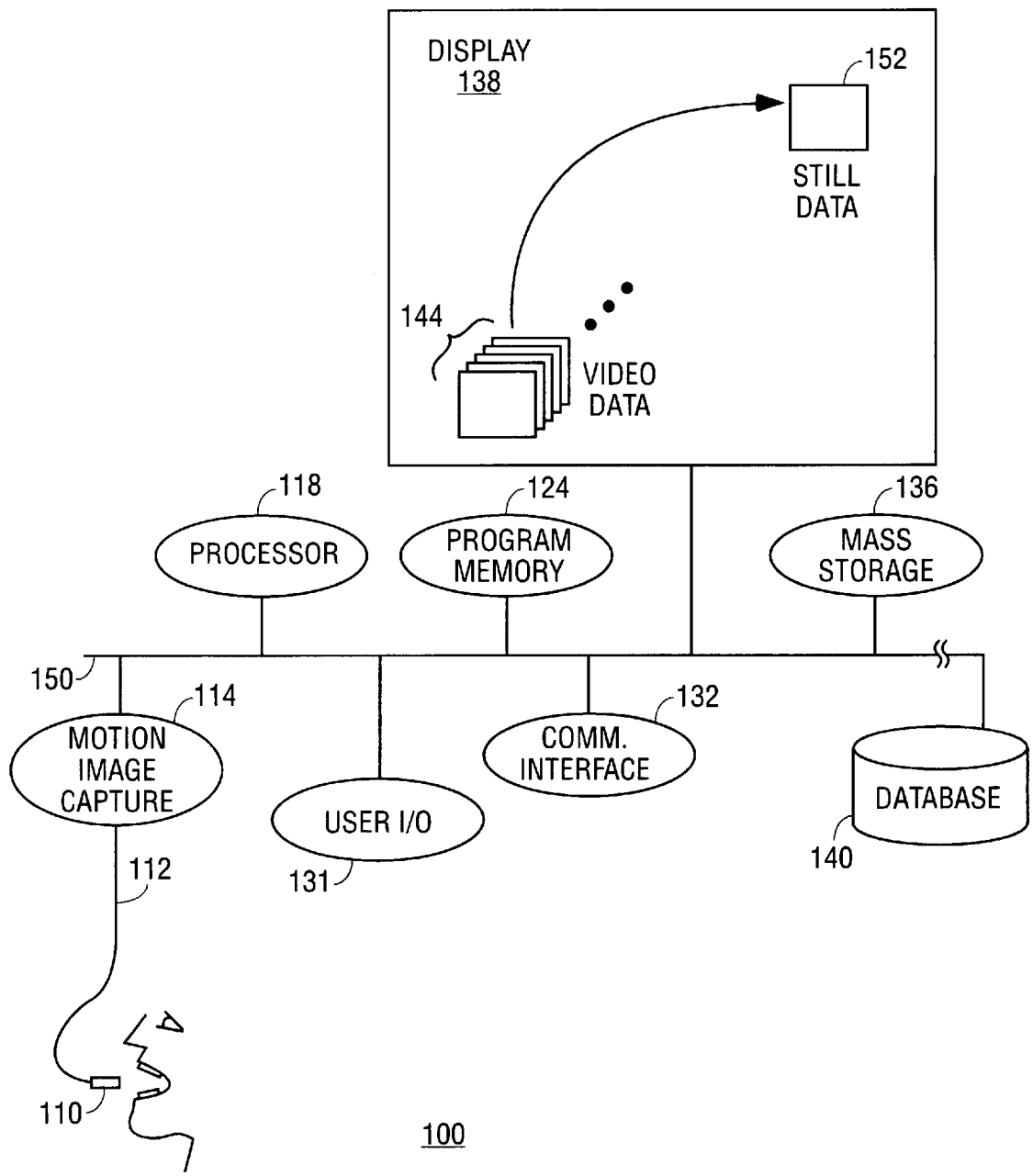
FIG. 1 is a logical block diagram of a computer system for digital motion and still image capture according to a first embodiment of the invention.
Figure 2:
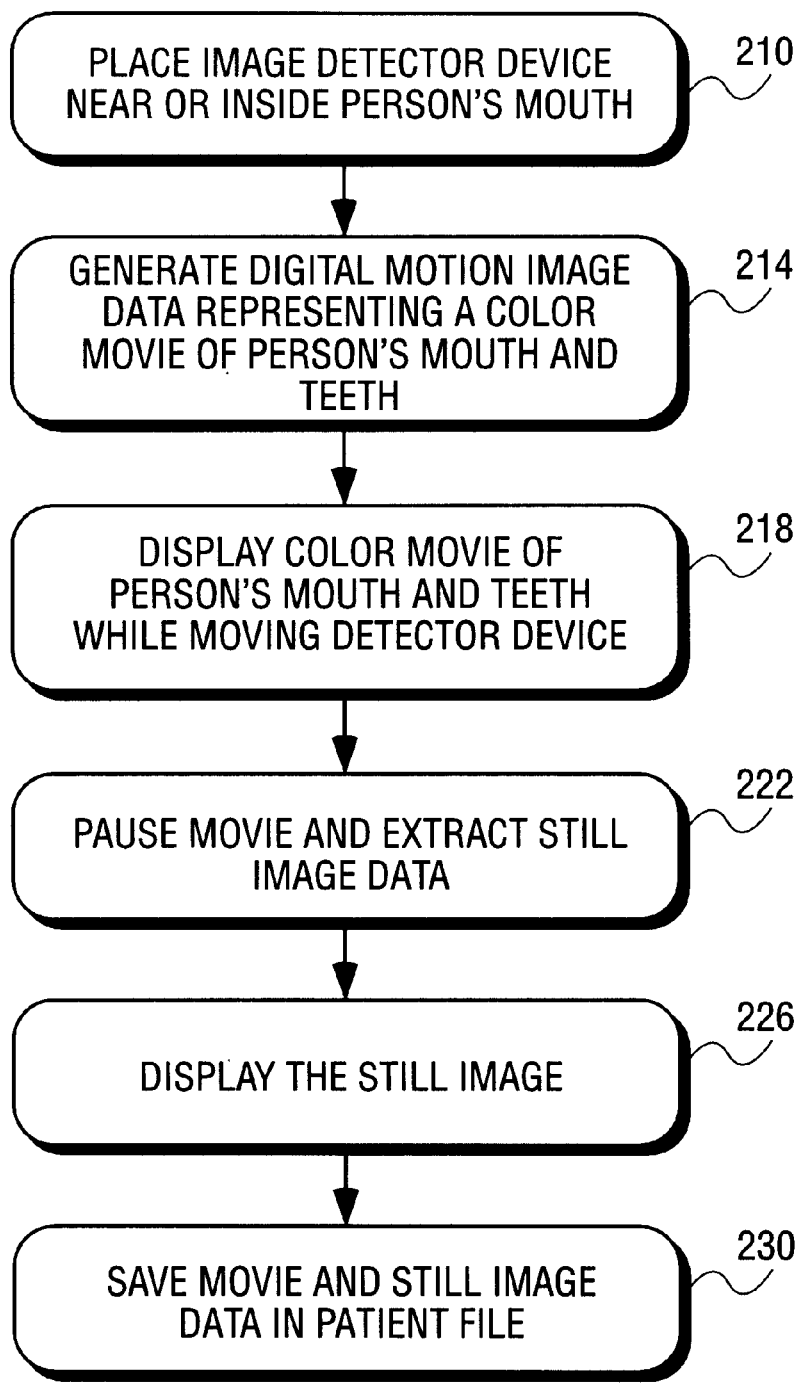
FIG. 2 is a flow diagram of steps performed during digital motion and still image capture according to another embodiment of the invention.

Turning now to the figures, FIG. 1 is a logical block diagram of a computer-based system 100 for digital motion and still image capture according to a first embodiment of the invention. In describing the system, the description below will also refer to the process steps in FIG. 2. The system 100 is built around a bus 150 and includes a processor 118 used for selecting still image data 152 from digital motion image data 144 that represent a movie of a patient's oral site. In one embodiment, the motion data are generated by a motion image capture block 114 in response to receiving signals from an image detecting device 110. The detecting device 110 may be a handheld device which includes an optical system and image sensor electronics that are configured to capture sufficiently detailed images of a person's oral site, including teeth and gums, for purposes of dental diagnosis. In one embodiment, the device is an intraoral camera which is partially inserted into a patient's mouth and aimed at the desired areas of the patient's oral site.

As the detecting device 110 is moved around the patient's mouth in step 210, motion data is being generated in step 214. The system displays the motion data as a movie to the user, and perhaps the patient, using a display 138, as part of step 218. A wide range of devices can be used as part of the display, including the conventional cathode ray tube (CRT), which have the proper spatial resolution and color capability for displaying detailed images of the mouth and teeth.

When an image of the desired area appears on the display 138, the user, in particular a dentist, selects data from the motion image data that represents a still image of the desired area. This may be done by first pausing the movie, and then selecting the paused image to be the still image, as performed in step 222. Motion data will normally continue to be recorded while the movie is paused, but need not be such as when the movie has already been previously recorded and is being played back. The movie may be paused in response to direct user input. The user input can be transmitted via a user I/O device 131 such as a foot pedal switch, a pointing device such as a mouse, or even a microphone if the computer system is configured to recognize voice commands. As an alternative to direct user input, the movie may be paused or a still image selected in response to a predefined triggering event. For instance, the processor can be programmed to pause the movie in response to detecting a particular pattern in the motion data. Thus, a wide range of mechanisms can be used to trigger pausing the movie.

Once the movie is paused, the user determines whether the paused image is of acceptable quality, i.e., sufficiently free of shakes or flutter. If the movie were playing in a small window, then the paused image can be enlarged and placed in a separate, larger window. Alternatively, if the computer system can support the needed frame rate while the movie is playing in a large window or even at the full resolution of the display, then the paused image need not be dragged or enlarged into a separate window. In either case, a still image of the desired area is displayed, as part of step 226.

Because of the rapid rate at which the motion data is acquired, the paused image is most likely free of flutter. In the event there is a noticeable shake or flutter, the user may quickly advance or rewind a few frames to obtain an alternate image that is free of shakes without repositioning the detecting device and re-recording a still image. The alternate image will most likely cover the desired area of the oral site, due to the high rate used in acquiring the motion data. Indeed, experimental results have shown, in one embodiment of the invention, a high likelihood of the first paused image having minimal or no perceptible shakes. The motion data in that case were obtained at a rate of approximately 12 frames/second. Higher frame rates may be possible, depending on the processing and storage capability of the processor 118 and motion image capture mechanism 114, which may further reduce the likelihood of the paused image being affected with shakes.

Once the desired tour of the patient's mouth has been recorded as a movie along with the derived still images, the recorded data associated with patient identification, and perhaps with other patient or treatment information, may be stored as part of a patient file as step 230. The determination of patient identification and other information for the patient file may be made prior, during, or after the motion and still data has been acquired. The patient file is a collection of one or more electronic files that contain movies and/or still images of a dental patient, such as a human being or animal, acquired by the system 100. The patient file can be stored as part of a database 140 which may include the patient files of a dental service provider or research institution. The database can be part of a computer network (not shown) in a dentist's office, so that in the embodiment of FIG. 1, the link between the database and the processor is a local area network (LAN) link. In addition, the database can be part of a larger intranet, enterprise network, wide area network, or even the Internet for access by an even greater number of users.

In addition to being stored in a database, the acquired motion and still data can also be transmitted in real-time to remote locations using an optional communication interface 132. For example, the interface may include a standard analog modem used to engage in videoconferencing with other dentists or specialists at remote locations over the telephone lines.

The embodiments of the invention described above may be implemented using a general purpose personal computer ("PC") of the Windows™/Intel™ ("Wintel") or of the Apple Macintosh™ variety. Of course, more specialized machines such as image processing-type workstations can also be used. The Wintel PC can feature an Intel Pentium processor running a Microsoft Windows graphical user interface. The system hardware can be centered around a Peripheral Components Interconnect (PCI) bus to which the processor, program memory 124 (which normally comprises mostly of semiconductor random access memory (RAM)), display, mass storage device 136 such as a magnetic and/or optical disk drive, and a motion image capture device 114 such as a digital video capture card or board are coupled. The video capture card can be one which supports Microsoft's Video for Windows suite of imaging and graphics protocols. The video capture card is coupled to the image detecting device being, for instance, an intraoral camera, via an analog signal interface 112 such as one that supports the industry standard S Video output. The video capture card will have the proper hardware (including logic circuitry and/or a programmed processor) to interface with the intraoral camera and to implement the function of an image frame grabber as known to those skilled in the art. The intraoral camera has an optical system and image sensor technology that are suitable for obtaining acceptable quality images of a patient's mouth and teeth for dental diagnosis purposes, as known to those skilled in the art.

The needed software for orchestrating image capture, display, and storage can be written using different programming languages and tools, such as the C language and the Microsoft Windows Application Programming Interface. An embodiment of the software architecture is illustrated in FIG. 3.

Figure 3:
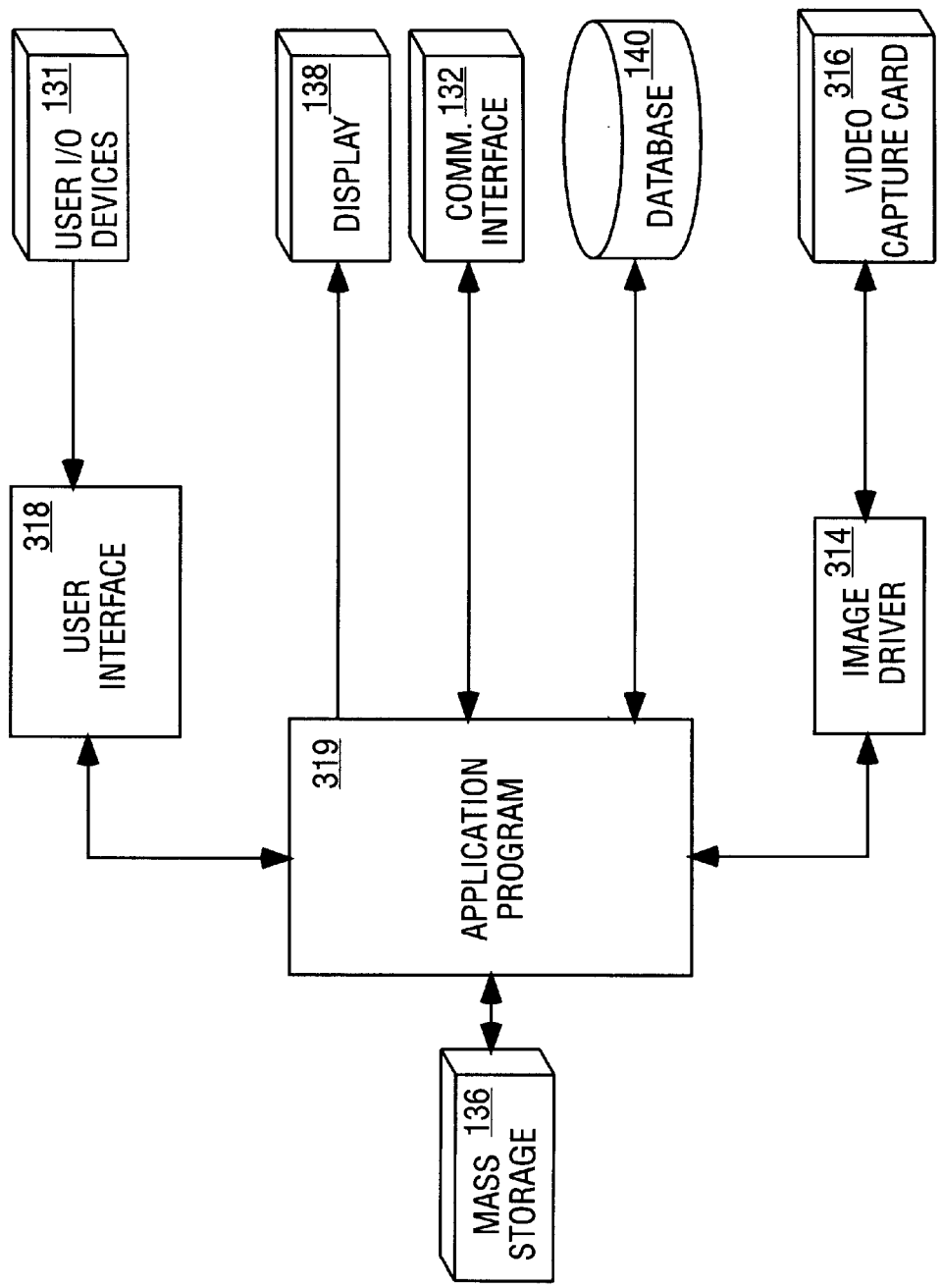
FIG. 3 illustrates an embodiment of the invention as a software/hardware architecture for digital motion and still image capture.

FIG. 3 illustrates a software and hardware architecture for an embodiment of the invention as a dental imaging system featuring motion and still image capture. The architecture includes three main software blocks entitled application program 310, user interface 318 and imaging driver 314. These components operate together to perform the necessary computer implemented steps of the flow diagrams in FIGS. 2 and 4.

The application program 310 may be configured as a stand-alone piece of software that can communicate with the different hardware components illustrated in order to orchestrate the functions of a dental imaging system, including image capture, display, and storage. In particular, image capture is performed with the aid of an imaging driver 314. The imaging driver 314 is a device driver, i.e., a piece of software used to control a hardware component or computer peripheral device, in this case the video capture card or board 316. The driver 314 forwards motion image data from the video capture board to the application program. In one embodiment, the imaging driver 314 may be a Video For Windows (VFW) driver provided by Microsoft Corporation and which is designed to interface a video capture card 316 supplied by a particular manufacturer. The VFW driver and corresponding video capture board support the VFW suite of protocols.

In addition to communicating with the imaging driver, the application program also communicates with a user interface 318. The user interface 318 obtains user commands in terms of foot pedal movement, cursor movement, and mouse select button/keyboard information from various I/O devices 131 such as a foot pedal actuator; mouse, track ball, keyboard, touch sensitive screen or other display pointing mechanism; and even a microphone for voice commands. The user commands include start movie, stop movie, and select and drag still image frame as well as any other display and program control commands which are used by the application to control the operation of the dental imaging system.

The application program 319 can be modeled based on an image capture test program known as CAPTEST which is often shipped with VFW to test the performance of the video capture card. The application program should be written to communicate with the imaging driver 314, mass storage 136, and display 138 to retrieve, save, and display the motion image data representing a patient exam movie. In addition, the application program should also include the ability to pause the movie while the motion image data is being recorded and extract a still image frame for the paused image. The results can be seen in an exemplary screen shot of a display illustrated in FIG. 5 in which a centrally located movie window 510 displays a paused image of a patient's tooth. In that embodiment, the movie can be paused using a control panel at the top of the window 510, and/or using a footpedal switch (not shown).

Figure 5:
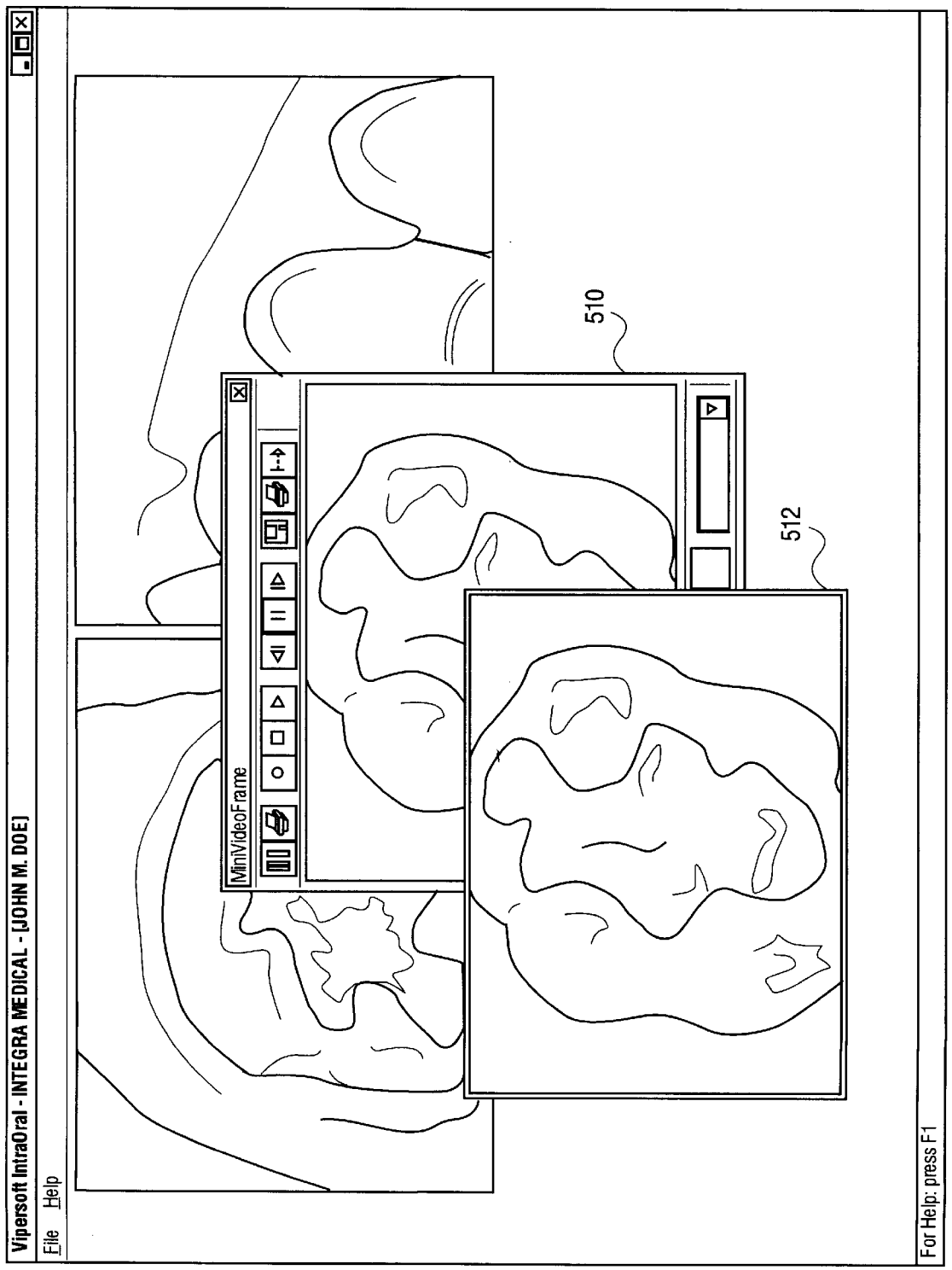
FIG. 5 illustrates a screen shot of a display showing still images in multiple windows according to another embodiment of the invention.

After the movie is paused, the user may select the movie window 510 containing the paused image 512 and drag the paused image towards a corner of the display. The application program 310 is configured to automatically expand or scale the paused image into a larger window that covers approximately one fourth of the full display. The user may next advance or rewind the movie, on a per frame basis if desired, using the control panel in the movie window 510 to display images of other treatment areas or alternate shake-free still images of the same area. These additional still images can also be selected and dragged to the remaining corners of the display as shown in FIG. 5. In this way, the user can effectively display multiple still images, based on the original patient exam movie, that show different areas of treatment in the patient's mouth in a shake-free manner.

The application program 310 also supports interfaces to the hardware communication interface 132 to perform, for instance, videoconferencing. In additional to being shared with others at remote sites, the images obtained by the application program can be stored in a database 140. In particular, the interface to the database 140 may be implemented based on Microsoft Access™ or other commercially available database programs that can support the storage and access of patient files that include the still image data as JPEG files and perhaps even the motion image data as MPEG and AVI movie files.

Although a particular embodiment using currently mature technologies has been described in reference to FIG. 1, it should be noted that other technologies can also be used which still retain the spirit of the invention. For instance, future sensor technologies may be developed which allow the image detecting device 110 to transfer digital signals, including perhaps the actual motion image data, directly to the system's processor 118, using, for instance a high performance computer peripheral bus interface (not shown) that operates according to standards such as Universal Serial Bus (USB) or IEEE 1394-1995. In that scenario, the digital functions of the motion image capture block 114 could be subsumed by either the processor 118 or the detecting device 110.

Another embodiment of the invention can be defined as computer-readable media. The medium can be, for instance, an optical disk such as a CD-ROM that contains different software components which represent and include instructions to be executed by the system and in particular the processor 118 of FIG. 1. The instructions cause the processor 118 to configure the system 100 to perform the steps described above in FIG. 2 or below in FIG. 4 to obtain still images derived from a digital movie. The medium can alternatively include an integrated circuit that is part of the program memory 124 (see FIG. 1) loaded with the instructions that configure the processor to perform the steps of FIG. 2 or FIG. 4 or with the software described in FIG. 3. A wide range of media storing the instructions are contemplated, including a distributed medium in which parts of the instructions appear in separate machines that are linked together through a network. The instructions stored in the media can, in addition to image capture, cause the system to perform a variety of image editing and transmitting (e.g., videoconferencing) functions as well.

Figure 4:
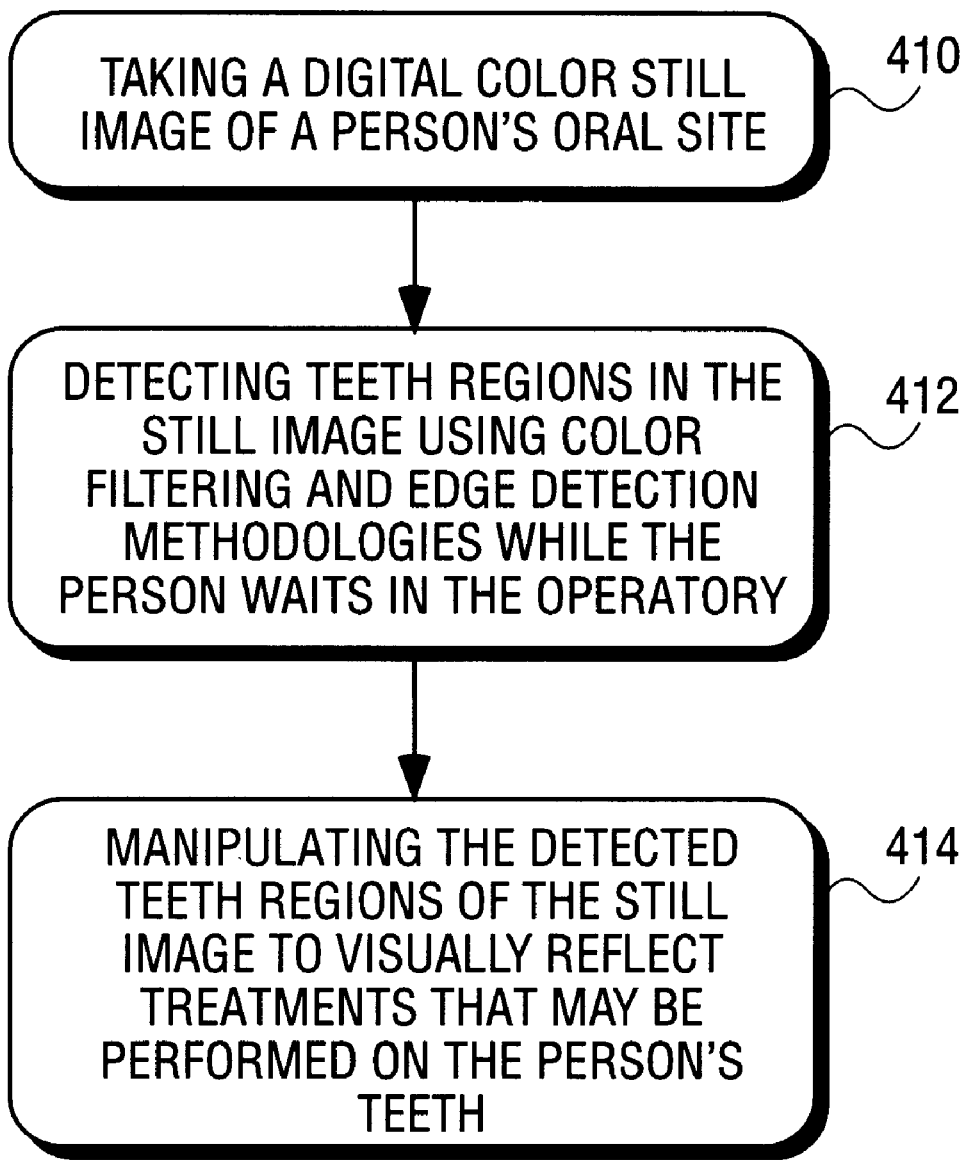
FIG. 4 illustrates a flow diagram of steps performed by a computer system for automatic tooth detection according to another embodiment of the invention.

Another embodiment of the invention is directed at using image processing techniques including color and edge detection to automatically detect regions having teeth in an image of a patient's mouth, without having to manually define the regions. The steps as illustrated in FIG. 4 begin with step 410 obtaining a still color image of the patient smiling or with her mouth open so that her teeth are visible. The still image can be obtained using, for instance, the techniques described above in connection with FIG. 2.

Figure 6:
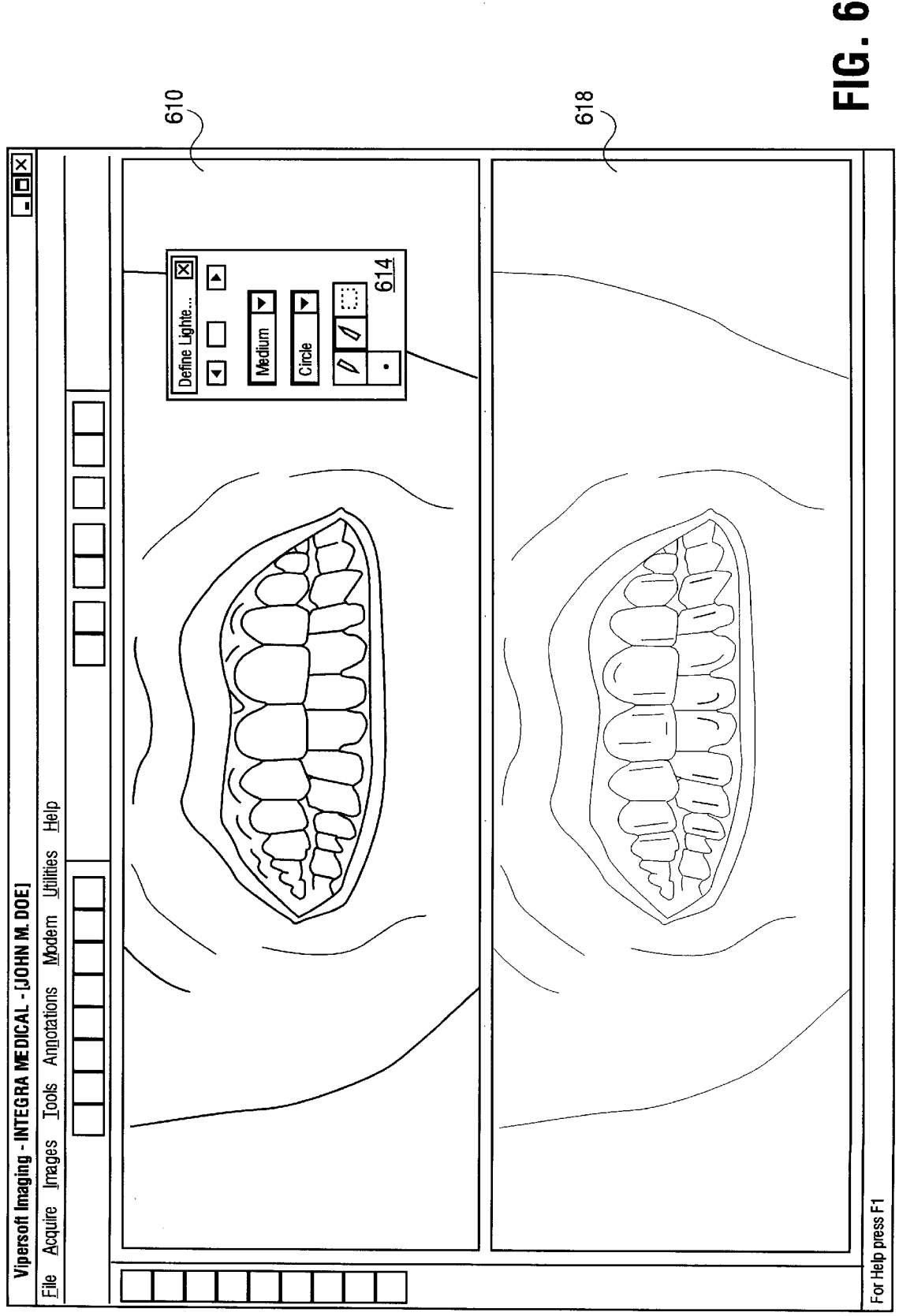
FIG. 6 illustrates a screen shot showing the results of the tooth detection methodology according to another embodiment of the invention.

Once the still image showing the teeth has been captured, the user may select an area of the image that contains one or more teeth by, for instance, drawing a rectangle around the patient's teeth. This defines a detection area in the bitmap image. Operation then continues with step 412 where the system is configured to scan the image data, including pixel values, in the selected area looking for predefined color and hue patterns and edge conditions that define teeth. An exemplary methodology for tooth detection described using pseudo-code is shown below together with an exemplary C language source code listing in Appendix A. A screen shot of the results that may be obtained is illustrated in FIG. 6 where image 610 is the original still image and image 618 includes the detected teeth regions being highlighted.

Pseudo Code for Automatic Tooth Detection

Elements:
1. Bitmap still image
2. Monochrome bitmap image (Mask)
3. Area of image to apply detection
4. Blue filter value. Percentage of blue vs. red (variable value)
5. Green filter value. Percentage of green vs. red (variable value)
6. Lower intensity level (variable value)
7. Upper intensity level (variable value)

Establish a Middle (average) intensity level:
e.g., Middle=(upper−lower)/2+lower
Establish tolerance level for intensity comparison:
e.g., Tolerance=(upper−lower)/2+1
Test each pixel for criteria:
3. Go through each row.
4. Go through each column.
5. Mark the mask if the following (a) and either (b) or (c) are true:
   (a) The [absolute value of a bitmap pixel value]−[a Middle value] is less than or equal to the Tolerance.
   (b) The red value of the bitmap pixel is less than the green filter value multiplied by the green value of the bitmap pixel.
   (c) The red value of the bitmap pixel is less than the blue filter value multiplied by the blue value of the bitmap pixel.

Optionally test for Best Detection. Elements:
1. Desired percentage of the selected detection area that should be filled with tooth region.

To perform best detection:
1. Calculate number of pixels in area of detection.
2. Keep count of number of marked bits in mask (tooth region).
3. Calculate the percentage of marked bits by taking the number of marked bits and dividing by the number of pixels in area of detection then multiplying by 100.
4. If the percentage is not sufficiently close to the desired percentage, adjust one or more of the following:
   (i) Upper intensity level.
   (ii) Lower intensity level.
   (iii) Blue filter value.
   (iv) Green filter value.
   (v) Middle (average) value (may be done by adjusting the upper and lower intensity levels).
   (vi) Tolerance value.
5. Repeat "Test each pixel for criteria" test (as described above).

Ending result—Mask filled in corresponding with the teeth in the bitmap image.

The example pseudo-code above is based on pixels having 3 colors red, green, and blue, although other color combinations (including monochrome) may be used. The lower and upper intensity levels serve to define a brightness range for detecting the teeth. The upper, lower, and the middle and tolerance values may each be obtained by sampling of the detection area for the statistically lowest and highest intensities. A statistical value may be used rather than the absolute lowest and highest intensities.

If the patient's teeth in the still image are particularly bright, then the upper and lower values may be altered to yield a larger Tolerance value for comparison, in order to capture the brighter pixels of the tooth region. If the still image is of very high resolution and color accuracy (such as images obtained from a photo CD which were obtained, for instance, using a high resolution scanner), then the color filter values may be altered to better capture the pixels near the edge between the tooth region and gum region. These adjustments may be performed manually by the user selecting and sliding a scroll bar 614 in FIG. 6, or they may be done automatically by an optimization routine (Best Detection in pseudo-code above). The results of the adjustments can be viewed by configuring the software to highlight the detected teeth regions, as shown in the separate image 618 of FIG. 6.

After the teeth regions have been differentiated from the gums and other parts of the patient's mouth, the regions can be graphically altered to show, for instance, the effect of teeth whitening or of the person's smile after cosmetic surgery, as part of step 414. The automatic tooth detection technique allows the imaging of cosmetic effects to be performed much more rapidly and accurately than with the conventional manual method. In a particularly desirable scenario, all of the steps of FIG. 4 are performed while the patient is lying on a chair in the operatory. This permits the "before and after images" to be produced without the patient having to leave her chair in the operatory, thus providing the patient with a more efficient and compelling service.

To summarize, the above-described embodiments of the invention are directed at methods and apparatus for improved dental imaging using digital motion video techniques to derive substantially shake-free still images of a person's mouth and teeth. The embodiments of the invention are, of course, subject to some variations in structure and implementation. For instance, the movie while being recorded as digital motion image data may be temporarily stored in the mass storage 136, or entirely in the program memory 124 if there is sufficient RAM in the program memory (see FIG. 1). Therefore, the scope of the invention should be determined not by the embodiments illustrated but by the appended claims and their legal equivalents.

APPENDIX A

```
/******************************************************************/
/*
/*    Functions included
/*
/*    mark_mask,
/*    range_test,
/*
/*    RangeLighten
/*
/*    Written by James W. Morandi
/*    Copyright (c) 1997 James W. Morandi
```

APPENDIX A-continued

```c
/*  This material is confidential
/*
*************************************************************/
// standard header files
#include <stdafx.h>
#include "imlead.h"
/***************************************************************
/*
/* mark_mask - marks a pixel in the mask at location (x,y)
/*
/* Input Parameters:
/*
/*   IMAGE *mask   - the mask to mark
/*   int x         - x coordinate of pixel to mark
/*   int y         - y coordinate of pixel to mark
/*
/* Returns:
/*   void
/*
/* Outputs:
/*   IMAGE *mask   - marked at location (x,y)
/*
***************************************************************/
void mark_mask(IMAGE *mask, int x,int y)
{
    int    bit;
    int    dx;
    unsigned char *p;
    dx = x - mask->r.o.x;
    bit = 0x80 >> (dx % 8);
    p = (unsigned char*)mask->base + ((mask->width * (y - mask->r.o.y)) +
        (dx/8)):
    *p |= bit;
}
/***************************************************************************
/*
/* range_test - perform actual testing of pixel against criteria
/*
/* input Parameters:
/*   RGB24 *ptr          - pointer to pixel to test
/*   PIXVAL *color       - pointer to test against tolerance and pixel
/*   int tol             - intensity tolerance value
/*   double dfGreenVal   - percentage to test green intensity against red
/*                         value
/*   double dfBlueVal    - percentage to test blue intensity against red
/*                         value
/*
/* Returns:
/*   TRUE if pixel passes criteria
/*   FALSE if pixel does not pass criteria
/*
/* Outputs:
/*   none
/*
***************************************************************************/
BOOL range_test(RGB24 *ptr, PIXVAL *color, int tol, double dfGreenVal,
                double dfBlueVal)
{
int    r1;
int    g1;
int    b1;
int    r2;
int    g2;
int    b2;
int    rd;
int    rd2;
    b1 = ptr->b;
    g1 = ptr->g;
    r1 = ptr->r;
    b2 = color->p24.b:
    g2 = color->p24.g;
    r2 = color->p24.r;
    rd = (r1+g1+b1)/3;
    rd2 = (r2+g2+b2)/3;
    if((abs(rd-rd2) <= tol) && ((r1 < (g1*dfGreenVal) || (r1 < b1*dfBlueVal)))
        return TRUE;
    else
        return FALSE;
}
```

APPENDIX A-continued

```
/****************************************************************************
/*RangeLighten - test each pixel and mark mask accordingly
/*
/* Input Parameters:
/*    IMAGE *im       -the image to test
/*    IMAGE *m        -the mask to mark
/*    IRECT rect      -the area in the image to test
/*    int iBlueFilter  -variable blue filter value
/*    int iGreenFilter -variable green filter value
/*    int iLiteLimit   - highest intensity value allowed in image (generally 255)
/*    int iDarkLimit   -lowest intensity value allowed in image (generally 0)
/*
/* Returns:
/*    void
/*
/* Outputs
/*    Image *m        -marked with matched pixels
/*
/*
****************************************************************************/
void RangeLighten(IMAGE *im, IMAGE *m, IRECT rect, int iBlueFilter,
        int iGreenFilter, int iLiteLimit, int iDarkLimit)
{
PIXVAL color;
int tol;    //tolerance
unsigned char cMid;
int x,y;
RGB24 *ptr;
double dfBlueVal, dfGreenVal;
        tol = (iLiteLimit - iDarkLimit)/2;
        cMid = tol + iDarkLimit; // get middle (average) value
        tol++;           // one mare than middle value
        color.p24.4 = color.p24.g = color.p24.b = cMid;
        dfBlueVal = iBlueFilter / (double) 100;
        dfGreenVal = iGreenFilter / (double)100;
        for(y=rect.o.y;y < rect.c.y;y++)
                {
                // go through each row
                ptr = (RGB24*) im->row_pixels[y];
                ptr += rect.o.x;
                for (x=rect.o.x;x < rect.c.x;x++)
                        {
                        // go through each pixel in the row and perform test
                        if (range_test(ptr++,& color, tol, dfGreenVal, dfBlueVal))
                                {
                                // passed test - mark mask
                                mark_mask(m,x,y);
                                }
                        }
                }
}
```

What is claimed is:

1. A method of dental imaging comprising
generating a plurality of digital images as a sequence representing a color movie of a patient's oral site based on signals received from an intraoral camera;
selecting one of the plurality of digital images that are being displayed as a still image of the site;
displaying the still image of the site; and
storing the still image data in a patient file.

2. A method as in claim 1 further comprising
associating the plurality of digital images with a patient identification; and
saving the plurality of digital images in the patient file.

3. A method as in claim 1 wherein the step of generating the plurality of digital images further comprises
receiving the plurality of digital images from a video capture card that is coupled to the intraoral camera.

4. A method as in claim 1 wherein the step of generating further comprises
receiving digital signals from the intraoral camera through a computer peripheral bus interface that correspond to a plurality of images depicting motion captured by the camera; and
deriving the plurality of digital images based on the received digital signals.

5. A method as in claim 1 wherein the patient's oral site is her teeth.

6. A computer-readable medium having a representation of instructions to be executed by a computer to perform the method of claim 1.

7. A method of dental imaging comprising
placing a portion of a handheld intraoral camera being held by a first person near a second person's oral site, the camera being configured to provide signals that represent sufficiently detailed color motion images of the site for dental diagnosis purposes;
generating a sequence of digital images in response to signals received from the camera;
displaying the sequence of digital images as a color movie of the oral site while moving the camera around the oral site;
pausing the movie to yield and display one of the sequence of digital images as a paused digital image of the site; and
storing the paused digital image in a patient file.

8. A method as in claim 7, further comprising after the step of pausing:

one of advancing and rewinding the paused movie at least one frame to obtain an alternate paused digital image; and storing the alternate paused digital image in the patient file.

9. A computer-implemented method of dental imaging comprising generating digital motion image data representing a color movie of a patient's oral site based on signals received from a handheld intraoral camera;

pausing the movie on a display to yield a still image while simultaneously continuing to generate the digital motion image data representing the color movie of the oral site;

displaying the still image of the site; and storing the still image data in a patient file.

10. A method of dental imaging comprising placing a portion of a handheld intraoral camera being held by a first person near a second person's oral site, the camera being configured to provide signals that represent sufficiently detailed color motion images of the site for dental diagnosis purposes;

generating digital motion image data in response to signals received from the camera;

displaying a color movie of the oral site based on the digital motion image data while moving the camera around the oral site;

pausing the movie to yield and display a paused digital image of the site;

one of advancing and rewinding the paused movie at least one frame to obtain an alternate digital image;

storing the alternate paused digital image in the patient file; and displaying the alternate digital image in a display window separate from the paused movie.

* * * * *